United States Patent [19]

Hays

[11] Patent Number: 5,482,964

[45] Date of Patent: Jan. 9, 1996

[54] SUBSTITUTED PHENOXYHYDROXYPROPYL AMINES AS CENTRAL NERVOUS SYSTEM AGENTS

[75] Inventor: Sheryl J. Hays, Ann Arbor, Mich.

[73] Assignee: Warner-Lambert Company, Morris Plains, N.J.

[21] Appl. No.: 321,291

[22] Filed: Oct. 11, 1994

[51] Int. Cl.$^6$ .................... A61K 31/135; C07C 217/60; C07C 323/32; C07C 323/38

[52] U.S. Cl. .......................... 514/415; 514/650; 514/652; 514/653; 564/338; 564/341; 564/349; 564/351

[58] Field of Search ................................ 564/338, 341, 564/349, 351; 514/419, 650, 652, 653

[56] References Cited

U.S. PATENT DOCUMENTS 3,857,891 12/1974 Holmes et al. ..................... 564/349
5,382,689 1/1995 Nomura ............................. 564/349

FOREIGN PATENT DOCUMENTS 2043216 11/1991 Canada .

OTHER PUBLICATIONS

Miyano et al, J. Org. Chem., vol. 50 (1985) pp. 4350–4360.
Runge et al, Chemical Abstracts, vol. 87 (1977) 134458k.

*Primary Examiner*—Richard L. Raymond
*Attorney, Agent, or Firm*—Todd M. Crissey; Francis J. Tinney

[57] ABSTRACT

Substituted phenoxyhydroxy amines and derivatives thereof are described as well as methods for the preparation and pharmaceutical compositions of same, which are central nervous system agents useful in the treatment of neurological disorders including traumatic brain surgery, stroke, migraine, acute and chronic pain, epilepsy, Parkinson's disease, Alzheimer's disease, amyotropic lateral sclerosis, multiple sclerosis, psychosis, and depression.

7 Claims, No Drawings

SUBSTITUTED PHENOXYHYDROXYPROPYL AMINES AS CENTRAL NERVOUS SYSTEM AGENTS

BACKGROUND OF THE INVENTION

The present invention relates to novel substituted phenoxyhydroxy amines and derivatives thereof useful as pharmaceutical agents, to methods for their production, to pharmaceutical compositions which include these compounds and a pharmaceutically acceptable carrier, and to pharmaceutical methods of treatment. The novel compounds of the present invention are useful in the treatment of neurological disorders such as traumatic brain injury, stroke, migraine, acute and chronic pain, epilepsy, Parkinson's disease, Alzheimer's disease, amyotropic lateral sclerosis, multiple sclerosis, psychosis, and depression.

It is well-established that an accumulation of calcium (calcium overload) in the brain is seen after anoxia, ischemia, migraine, and other hyperactivity periods such as after epileptic convulsions. An uncontrolled high concentration of calcium in neurons of the central nervous system (CNS) is known to cause most of the degenerative changes connected with the above disease states. Therefore, compounds which block the calcium channels of brain cells will be useful in the treatment of neurological disorders such as brain injury, stroke, migraine, acute and chronic pain, epilepsy, Parkinson's disease, Alzheimer's disease, amyotropic lateral sclerosis, multiple sclerosis, and the neurodegeneration associated with the same.

Compounds which partially or completely block sodium or calcium channels will be useful for the treatment of the above disorders by indirectly or directly blocking the calcium influx into the CNS. L-channel antagonists such as nimodipine (Gelmers H. J., et al., *New England Journal of Medicine*, 318:203–207 (1988)) and dual sodium/calcium channel antagonists such as phenytoin (Kinouchi H., et al., *Stroke*, 21:1326–1330 (1990)) have demonstrated antiischemic and anticonvulsant activities in animal and clinical studies.

It is also known that N- and P-type calcium channels are involved with the regulation of neurotransmitter release. Subtype-specific neuronal calcium blockers are antinociceptive in rodent models of painful peripheral neuropathy. Voltage-sensitive calcium channel blockers prevent pain behavior elicited by tactile stimulation in animals with permanent peripheral nerve injuries. The calcium channel blocker, SNX-111, has demonstrated activity in several rodent models of acute and chronic pain (Bowersox S. S., et al., *Drug News and Perspective*, 7:261–268 (1994)). Enhanced neurotransmitter release of glutamate, aspartate glycine, dopamine, and serotonin may contribute to the etiology of many neurological disorders. Blockade of neurotransmitter release may, therefore, be useful in the treatment of pain, psychosis, Parkinsonism, depression, epilepsy, and other convulsive disorders.

Canadian Patent Application CA 2,043,216 discloses compounds of Formula III

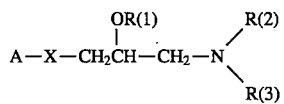

and of their salts with pharmaceutically acceptable acids and also of pharmaceutical preparations containing these compounds III for the production of a medicament for the prevention of and for the treatment of fungal diseases, the radicals in Formula III having the following meaning:

R(1) is H, $(C_1-C_3)$-alkyl (straight-chain or branched), $(C_2-C_{18})$-alkenyl (straight-chain or branched, mono- or polyunsaturated), benzyl, [unsubstituted or mono- or polysubstituted by F, Cl, Br, $CF_3$, $(C_1-C_4)$-alkyl (straight-chain or branched), $OCH_3$, O-phenyl or phenyl], $C(O)$-$(C_1-C_6)$-alkyl (straight-chain or branched), or C(O)-phenyl, R(2) is H, $(C_1-C_{18})$-alkyl (straight-chain or branched), $(C_1-C_6)$-alkloxy-$(C_1-C_6)$-alkyloxy (straight-chain or branched), $(C_1-C_6)$-alkyloxyphenyl (straight-chain or branched), $(C_2-C_{18})$-alkenyl (straight-chain or branched, mono- or polyunsaturated), $(C_3-C_{12})$-cycloalkyl (mono-, bi-, or multicyclic, such as norbornyl, adamantyl, or decahydronaphthalenyl), phenyl-$(C_1-C_6)$-alkyl (straight-chain or branched, the alkyl chain being unsubstituted or mono- or disubstituted by OH), phenyl-$(C_2-C_6)$-alkenyl (straight-chain or branched, mono- or polyunsaturated), diphenyl-$(C_1-C_6)$-alkyl (straight-chain or branched) or phenyl, the phenyl systems being unsubstituted or mono- or polysubstituted by substituents from the group comprising F, Cl, Br, $(C_1-C_{18})$-alkyl (straight-chain or branched), $(C_2-C_{20})$-cycloalkyl, OH, SH, $(C_1-C_{18})$-alkoxy (straight-chain or branched), $(C_1-C_4)$-alkylenedioxy (straight-chain or branched), dimethylaminoethoxy, $(C_1-C_4)$-alkoxycarbonylmethoxy (straight-chain or branched), phenoxy, phenyl, benzyl, phenethyl, thiophenyl, and $C_2F_{2n+1}$ where n is equal to 1–6, or R(2) is an indol-3-yl-$(C_1-C_4)$-alkyl radical (straight-chain or branched), thienyl, thienylmethyl, the thienyl radical being unsubstituted or substituted by F, Cl, $(C_1-C_4)$-alkyl or $O(C_1-C_4)$-alkyl (straight-chain or branched), R(3) is defined as R(2), R(2) and R(3) each having the same or a different meaning, or R(2) forms a —$(CH_2)_n$-chain with R(3) where n is equal to 4–6, in which a $CH_2$ group can be replaced by oxygen, sulfur or nitrogen, the additional nitrogen carrying a hydrogen atom, a $CH_3$, phenyl, benzyl or a phenethyl group as a further bonding component, and A is $(C_1-C_{18})$-alkyl (straight-chain or branched), $(C_2-C_{18})$-alkenyl (straight-chain or branched, mono- or polyunsaturated) or a group of the Formula II

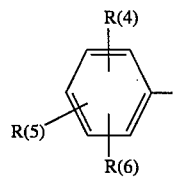

in which the radicals R(4), R(5), and R(6) have the following meaning:

R(4) is H, $(C_1-C_{18})$-alkyl (straight-chain or branched), $(C_2-C_{18}$-alkenyl (straight-chain or branched, mono- or polyunsaturated), $(C_3-C_{20})$-cycloalkyl, [mono-, bi-, or multicyclic, unsubstituted or mono- or disubstituted by $(C_1-C_4)$-alkyl (straight-chain or branched), $(C_1-C_4)$-alkoxy (straight-chain or branched), $C_2F_{2n+1}$ where n is equal to 1–4, F, Cl, Br, or OH], Y—$(C_1-C_{20})$-alkyl (straight-chain or branched), Y—$(C_2-C_{18})$-alkenyl (straight-chain or branched, mono- or polyunsaturated), Y—($C_3$–$C_{20}$)-cycloalkyl (mono-, bi-, or multicyclic, unsubstituted or substituted as indicated above), phenyl, Y-phenyl, phenyl-($C_1$–$C_4$)-alkyl (straight-chain or branched), phenyl-($C_1$–$C_4$)-alkoxy (straight-chain or branched), biphenylyl, F, Cl, Br, $C_nF_{2n+1}$ (where n is equal to 1–8), $CCl_3$, YH, naphthyl, CH or $NO_2$, the phenyl systems being unsubstituted or mono- or disubstituted by F, Cl, $CF_3$, ($C_1$–$C_4$)-alkyl (straight-chain or branched), or ($C_1$–$C_4$)-alkoxy (straight-chain or branched), where Y is equal to oxygen or sulfur, SO or $SO_2$, R(5) is defined as R(4), R(4) and R(5) being identical or different, or R(4) together with R(5) forms a $(CH_2)_p$ chain where p is equal to 3 or 4 in the case in which the substituents are bonded to adjacent positions on the phenyl ring, and R(6) is H, ($C_1$–$C_{15}$)-alkyl (straight-chain or branched), ($C_2$–$C_{15}$)-alkenyl (straight-chain or branched, mono- or polyunsaturated), Y—($C_1$–$C_{15}$)-alkyl (straight-chain or branched), Y—($C_2$–$C_{15}$)-alkenyl (straight-chain or branched, mono- or polyunsaturated), phenyl, Y-phenyl, benzyl, biphenylyl, F, Cl, Br, I, $C_nF_{2n+1}$ (where n is equal to 1–8), $CCl_3$, naphthyl or YH, and X is oxygen or sulfur for use in the prevention and treatment of fungal diseases.

However, the compounds disclosed in CA 2,043,216 do not specifically disclose or suggest the compounds of the present invention described hereinafter.

SUMMARY OF THE INVENTION

Accordingly, the present invention is a compound of Formula I

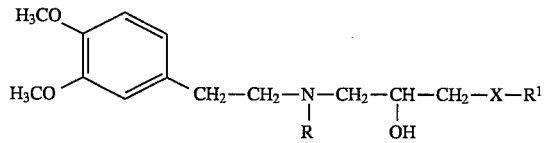

wherein

R is alkyl, arylalkyl, cyclohexylmethyl, or indol-3-ylmethyl;

$R^1$ is

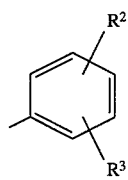

wherein $R^2$ and $R^3$ are each the same or different and each is hydrogen, alkyl, alkoxy, benzyloxy, cycloalkyl, halogen, or trifluoromethyl,

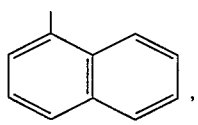

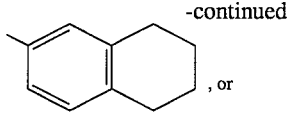, or

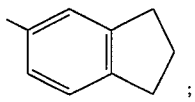;

X is O or S; and isomers thereof; or a pharmaceutically acceptable salt thereof.

As central nervous system agents, the compounds of Formula I are useful in the treatment of neurological disorders such as traumatic brain injury, stroke, migraine, acute and chronic pain, epilepsy, Parkinson's disease, Alzheimer's disease, amyotropic lateral sclerosis, multiple sclerosis, psychosis, and depression.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "cycloalkyl" means a saturated hydrocarbon ring having 5 to 6 carbon atoms and includes, for example, cyclopentyl, cyclohexyl, and the like.

The term "alkoxy" means alkyl—O— of from 1 to 6 carbon atoms as defined above for "alkyl."

The term "aryl" means an aromatic radical which is a phenyl group, a phenyl group substituted by 1 to 4 substituents selected from alkyl as defined above, alkoxy as defined above, halogen as defined hereinafter, trifluoromethyl, or nitro, a naphthyl group, or a naphthyl group substituted by 1 to 4 substituents selected from alkyl as defined above, alkoxy as defined above, halogen as defined hereinafter, or nitro.

The term "arylalkyl" means an aromatic radical, as defined above, attached to an alkyl group as defined above.

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

"Noble metal" is platinum, palladium, rhodium, ruthenium, and the like.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate [see, for example, Berge S. M., et al., "Pharmaceutical Salts," *Journal of Pharmaceutical Science*, 66:1–19 (1977)].

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all enantiomeric and epimeric forms as well as the appropriate mixtures and racemates thereof.

A preferred compound of Formula I is one wherein

R is methyl, arylalkyl, cyclohexylmethyl, or indol-3-ylmethyl;

$R^1$ is

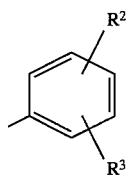

wherein $R^2$ and $R^3$ are each the same or different and each is alkyl, benzyloxy, cycloalkyl, or trifluoromethyl,

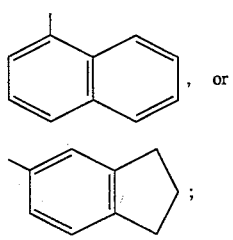, or

;

X is O or S.
Particularly valuable are:

1-[[2-(3,4-Dimethoxyphenyl)-ethyl]-(4-fluorobenzyl)-amino] -3-m-tolyloxy-propan-2-ol;

1-{Benzyl-[2-(3,4-dimethoxyphenyl)-ethyl]-amino}-3-m-tolyloxy-propan-2-ol;

1-{(4-Chlorobenzyl)-[2-(3,4-dimethoxyphenylethyl]-amino}-3-m-tolyloxy-propan-2-ol;

1-[[2-(3,4-Dimethoxyphenyl)-ethyl]-(3-fluorobenzyl)-amino]-3-m-tolyloxy-propan-2-ol;

1-[[2-(3,4-Dimethoxyphenyl)-ethyl]-(4-nitrobenzyl)-amino]-3-m-tolyloxy-propan-2-ol;

1-[[2-(3,4-Dimethoxyphenyl)-ethyl]-(3-nitrobenzyl)amino] -3-m-tolyloxy- propan-2-ol;

1-{(3-Chlorobenzyl)-[2-(3,4-dimethoxyphenyl)ethyl]-amino}-3-m-tolyloxy-propan-2-ol;

1-[[2-(3,4-Dimethoxyphenyl)-ethyl]-(4-methoxybenzyl)-amino]-3-m-tolyloxy-propan-2-ol;

1-{[2-(3,4-Dimethoxyphenyl)-ethyl]-naphthalen-1-ylmethylamino}-3-m-tolyloxy-propan-2-ol;

1-[[2-(3,4-Dimethoxyphenyl)-ethyl]-(3-methoxybenzyl)-amino]-3-m-tolyloxy-propan-2-ol;

1-[[2-(3,4-Dimethoxyphenyl)-ethyl]-(2-nitrobenzyl)amino] -3-m-tolyloxy-propan-2-ol;

1-[[2-(3,4-Dimethoxyphenyl)-ethyl]-(2-methoxybenzyl)amino]-3-m-tolyloxy-propan-2-ol;

1-[[2-(3,4-Dimethoxyphenyl)-ethyl]-(2-fluorobenzyl)amino]-3-m-tolyloxy-propan-2-ol;

1-{Benzyl-[2-(3,4-dimethoxyphenyl)-ethyl]-amino}-3-(4-benzyloxyphenoxy)-propan-2-ol;

1-{Benzyl-[2-(3,4-dimethoxyphenyl)-ethyl]-amino}-3-(4-cyclohexyl-2-methylphenoxy)-propan-2-ol;

1-{Benzyl-[2-(3,4-dimethoxyphenyl)-ethyl]-amino}-3-(indan-5-yloxy)-propan-2-ol;

1-{(2-Chlorobenzyl)-[2-(3,4-dimethoxyphenyl)ethyl]-amino}-3-m-tolyloxy-propan-2-ol;

1-{Benzyl-[2-(3,4-dimethoxyphenyl)-ethyl]-amino}-3-(naphthalen-1-yloxy)-propan-2-ol;

1-{Benzyl-[2-(3,4-dimethoxyphenyl)-ethyl]-amino}-3-(naphthalen-1-ylsulfanyl)-propan-2-ol;

1-{Benzyl-[2-(3,4-dimethoxyphenyl)-ethyl]-amino}-3-(3-trifluoromethylphenoxy)-propan-2-ol;

1-{Benzyl-[2-(3,4-dimethoxyphenyl)-ethyl]-amino}-3-(3-trifluoromethylphenylsulfanyl)-propan-2-ol;

1-{[2-(3,4-Dimethoxyphenyl)-ethyl]-phenethylamino}-3-m-tolyloxy-propan-2-ol;

1-{Cyclohexylmethyl-[2-(3,4-dimethoxyphenyl)ethyl]-amino}-3-m-tolyloxy-propan-2-ol;

1-(4-Cyclohexyl-2-methylphenoxy)-3-{[2-(3,4-dimethoxyphenyl)-ethyl]-methylamino}-propan-2-ol;

1-{[2-(3,4-Dimethoxyphenyl)-ethyl]-methylamino}-3-m-tolyloxy-propan-2-ol;

1-(4-Benzyloxyphenoxy)-3-{[2-(3,4-dimethoxyphenyl)ethyl]-methylamino}-propan-2-ol;

1-{[2-(3,4-Dimethoxyphenyl)-ethyl]-methylamino}-3-(indan-5-yloxy)-propan-2-ol;

1-{[2-(3,4-Dimethoxyphenyl)-ethyl]-methylamino}-3-(naphthalen-1-yloxy)-propan-2-ol;

1-{[2-(3,4-Dimethoxyphenyl)-ethyl]-methylamino}-3-(naphthalen-1-ylsulfanyl)-propan-2-ol; and 1-[[2-(3,4-Dimethoxyphenyl)-ethyl]-(1H-indol-3-ylmethyl)-amino]-3-m-tolyloxy-propan-2-ol; isomers thereof;

or a pharmaceutically acceptable salt thereof.
Most particularly valuable are:

1-(4-Cyclohexyl-2-methylphenoxy)-3-{[2-(3,4dimethoxyphenyl)-ethyl]-methylamino}-propan-2-ol;

1-{Benzyl-[2-(3,4-dimethoxyphenyl)-ethyl]-amino}-3-(4-cyclohexyl-2-methylphenoxy)-propan-2-ol; and 1-{Cyclohexylmethyl-2-(3,4-dimethoxyphenyl)ethyl]-amino}-3-m-tolyloxy-propan-2-ol; isomers thereof;
or a pharmaceutically acceptable salt thereof.

The compounds of Formula I are valuable central nervous system agents. The tests employed indicate that compounds of Formula I may possess activity useful for the treatment of neurological disorders.

A large influx of calcium from extracellular compartments into neurons is observed after opening of voltage-dependent calcium channels. The opening of calcium channels may be induced by a $K^+$-stimulated depolarization of neuronal membranes. A crude synaptosomal preparation contains small vesicles surrounded by neuronal membranes, and it is feasible to study the opening of voltage-operated calcium channels in such a preparation. In the test described below, the influx of $^{45}Ca^{++}$ into rat synaptosomes is studied under depolarized conditions. The effect of the test compounds on the depolarization induced calcium update can thus be studied. The calcium influx measured in this assay is believed to represent the P-type calcium channels.

Inhibition of [$^3$H]batrachotoxinin (BTX) binding to sodium channels in rat brain preparations has been used to detect compounds with affinity for sodium channels. Previous studies have shown that local anesthetics markedly inhibit [$^3$H]BTX binding in neuronal membrane preparations, and that this measure was a useful index for comparing potencies within a given chemical series. In this study, compounds were tested to inhibit [$^3$H]BTX binding in rat neocortical membranes.

The ability of the compounds to block sodium influx (NaFl) in CHO cells expressing the α subunit of rat brain Type IIa sodium channels was determined on a CNaIIA-1 cell line. The cells were treated with veratridine in the presence of α-scorpion toxin, which resulted in opening of the sodium channels. Inhibition of the [$^{14}$C]guanidinium influx was used to measure sodium channel blockade and the $IC_{50}$ values for compounds were determined.

Neocortical synaptosome preparation

Male rats (Sprague-Dawley, 200–220 g) were killed by decapitation and neocortices were isolated by blunt dissection. White matter was dissected away and the gray matter was placed in cold sucrose buffer (composition (mM): sucrose 320, TRIS base 5.0, EDTA 0.1; adjusted to pH 7.3 with HCl). The tissue was homogenized using 5 strokes at 500 rpm followed by 4 strokes at 800 rpm. The homogenate was centrifuged at 1075 g for 10 minutes. The pellet was discarded and the supernatant was centrifuged at 15800 g for 10 minutes at 4° C., and the supernatant was discarded. The final pellet was resuspended in incubation buffer and kept on ice.

Inhibition of depolarization induced $Ca^{++}$ flux (CaFl)

Fifty-microliter aliquots of neocortical synaptosome suspension were preincubated for 5 minutes at 25° C. in 400 µL of incubation buffer containing drug or control solvent. The synaptosomes were then exposed to a tracer quantity of $^{45}CaCl_2$ (1 µCi/mL) in combination with either 3 mM KCl (basal calcium flux or 30 mM KCl (stimulated calcium flux). The calcium flux was terminated by filtration over glass-fiber filters (GFB) using a Skatron 12-well harvester; filters were washed with a pressurized, continuous flow of 3 mL wash buffer (composition (mM): choline chloride 140, EGTA 3, HEPES 22; adjusted to pH 7.3 with TRIS base). Radioactivity of the filters was measured by scintillation counting. Basal calcium flux was subtracted from stimulated calcium flux in both control- and drug-treated conditions, and data were expressed as percent inhibition of the adjusted control response.

[$^3$H]Batrachotoxinin binding assay (BTX)

Male rats (Sprague-Dawley, 200–220 g) were killed by decapitation; neocortices were isolated by blunt dissection, cleaned of white matter, pooled and homogenized in ice-cold 50 mM HEPES-NaOH buffer (pH=7.4 at 22° C.) with a tissue homogenizer (Position 6, 30 seconds; Polytron, PTA 20 S) and centrifuged at 1000×g for 10 minutes at 5° C. The resultant supernatant was centrifuged at 4800×g for 10 minutes at 5° C. This step was repeated once more after resuspending the pellet in fresh buffer. The final pellet was suspended in fresh buffer and homogenized with a glass/Teflon homogenizer (800 rpm, 8 strokes; Potter Elvehjem). The resultant suspension was frozen rapidly and stored in liquid nitrogen, until it was used. In the [$^3$H]batrachotoxinin binding assay, incubation mixtures (250 µL) consisted of 100 µL of 50 mM HEPES-NaOH buffer (pH=7.4), 50 µL membrane suspension (~25 µg of protein), 25 µL tetrodotoxin (final concentration 1 µM), 25 µL scorpion venom (final concentration 5 µg/mL), 25 µL of either assay buffer (for total binding) or a solution containing interacting substance or aconitine (final concentration of 100 µM for nonspecific binding), and 25 µL of [$^3$H]batrachotoxinin (final concentration of 5 nM; 2.04 TBq/mmol). Incubations were terminated after 30 minutes at 37° C. by rapid filtration through presoaked (0.1% PEI) glass-fiber filters (GFC). The filters were immediately rinsed with three 4 mL volumes of ice-cold buffer. Radioactivity of the filters was measured by a liquid scintillation counter at the efficiency of 51%. Specific binding of [$^3$H]batrachotoxinin was defined as the difference between total and nonspecific binding. The results of competition experiments were analyzed by nonlinear curve-fitting algorithms, and they are expressed as $K_i$s according to the Cheng-Prusoff equation.

Inhibition of Veratridine-induced $Na^+$ influx (NaFl)

These experiments were performed using the cell line CNaIIA-1, derived from a Chinese Hamster ovary (CHO) cell line (CHO-K1; American Type Cultures) which were transfected with the vector ZEM2580 containing a cDNA encoding the rat brain IIA $Na^+$ channel (Scheuer T., et al., Science, 247:854–858 (1990); West J. W., et al., Neuron, 8:59–70 (1992)). The rat IIA sequence used contains the natural leucine at position 860, conferring normal voltage-dependent properties. CNaIIA-1 cells were cultured in 12-well plates at 37° C. and 5% $CO_2$ in RPMI medium 1640 (GIBCO) containing 10% fetal calf serum, 2 mL geneticin solution (5 mg/1 mL) and penicillin/streptomycin (final concentration 20 units/mL of penicillin G sodium and 20 µg/mL streptomycin sulfate). Incubation experiments were run on 500 µL scale by first adding 425 µL freshly oxygenated KRH buffer (pH=7.4), 25 µL drug solution in DMSO/$H_2O$:1/9 (final concentrations were ranging from 0.01 µM to 100 µM), 25 µL of a 0.6 mM veratridine solution (final concentration 30 µM) containing 0.124 µL α-scorpion venom solution (prepared by dissolving 5 mg α-scorpion venom in a mixture of 200 µL DMSO, 100 µL $H_2O$, and 100 µL of a 2.9N aqueous HCl) followed by an 11-minute incubation at 37° C. in a 5% $CO_2$ incubator, and finally, 25 µL [$^{14}$C]guanidine containing KRH buffer solution was added (final concentration 250 µM of "cold" guanidine and 0.005 µCi of [$^{14}$C]guanidine). The KRH (Krebs-Ringer HEPES) buffer used contained KCl (final concentration 4.75 mM); CaCl$_2$ (1.25 mM), KH$_2$PO$_4$ (1.20 mM), MgSO$_4$ (1.18 mM), HEPES (22 mM), dextrose (11 mM), and choline hydrochloride (130 mM). The pH of the buffer was brought to 7.4 with a 3M TRIS solution. The buffer was refrigerated and made fresh every week. The 0.6 mM veratridine was prepared by dissolving veratridine in equal volumes of 0.1N HCl and 0.1N NaOH and few drops of 1N HCl, followed by the addition of an a-scorpion venom solution (3.1 µg/mL). The drug solutions were prepared by dissolving the appropriate amount of either the salt or the free base of the drug to a 10% solution of DMSO in H$_2$O so that the final concentration of drugs ranged from 0.01 µM to 100 µM. The control solution contained equal volumes of 0.1N HCl and 0.1N NaOH. The experiments were terminated 25 minutes after the first addition (KRH buffer) by washing the wells containing the cell cultures with PBS buffer (2×2 mL) then adding a 3% solution of Triton X-100 (0.5 mL) and 30 minutes later tile well contents were transferred to a scintillation vial containing 10 mL of a Ready Gel scintillation solution with the amount of radioactivity remaining determined using a scintillation counter.

The data in Table 1 shows the central nervous system activity of representative compounds of Formula I.

TABLE 1

Biological Activity of Compounds of Formula I

| Example | Compound | CaFl (µM) | BTX Binding (µM) | NaFl (µM) |
|---|---|---|---|---|
| 1 | 1-[[2-(3,4-Dimethoxyphenyl)-ethyl]-(4-fluorobenzyl)-amino]-3-m-tolyloxy-propan-2-ol | 5.2 (N = 1) | | |
| 2 | 1-{Benzyl-[2-(3,4-dimethoxyphenyl)-ethyl]-amino}-3-m-tolyloxy-propan-2-ol | 9.2 (N = 3) | 0.52 (N = 1) | 8.9 |
| 3 | 1-{(4-Chlorobenzyl)-[2-(3,4-dimethoxyphenyl-ethyl]-amino}-3-m-tolyloxy-propan-2-ol | 77% at 30 µM<br>44% at 10 µM | | |
| 4 | 1-[[2-(3,4-Dimethoxyphenyl)-ethyl]-(3-fluorobenzyl)-amino]-3-m-tolyloxy-propan-2-ol | 6.6 (N = 1) | | |
| 5 | 1-[[2-(3,4-Dimethoxyphenyl)-ethyl]-(4-nitrobenzyl)-amino]-3-m-tolyloxy-propan-2-ol | 62% at 30 µM<br>59% at 10 µM | | |
| 6 | 1-[[2-(3,4-Dimethoxyphenyl)-ethyl]-(3-nitrobenzyl)-amino]-3-m-tolyloxy-propan-2-ol | 62% at 30 µM<br>57% at 10 µM | | |
| 7 | 1-{(3-Chlorobenzyl)-[2-(3,4-dimethoxyphenyl)-ethyl]-amino}-3-m-tolyloxy-propan-2-ol | 47% at 10 µM | | |
| 8 | 1-[[2-(3,4-Dimethoxyphenyl)-ethyl]-(4-methoxybenzyl)-amino]-3-m-tolyloxy-propan-2-ol | 5.4 (N = 1) | 0.152 | |
| 9 | 1-{[2-(3,4-Dimethoxyphenyl)-ethyl]-naphthalen-l-ylmethylamino}-3-m-tolyloxy-propan-2-ol | 9.9 (N = 1) | | |
| 10 | 1-[[2-(3,4-Dimethoxyphenyl)-ethyl]-(3-methoxybenzyl)-amino]-3-m-tolyloxy-propan-2-ol | 5.1 (N = 2) | | |
| 11 | 1-[[2-(3,4-Dimethoxyphenyl)-ethyl]-(2-nitrobenzyl)-amino]-3-m-tolyloxy-propan-2-ol | 3.1 (N = 1) | | |
| 12 | 1-[[2-(3,4-Dimethoxyphenyl)-ethyl]-(2-methoxybenzyl)-amino]-3-m-tolyloxy-propan-2-ol | 4.1 (N = 1) | | |
| 13 | 1-[[2-(3,4-Dimethoxyphenyl)-ethyl]-(2-fluorobenzyl)-amino]-3-m-tolyloxy-propan-2-ol | 1.8 (N = 2) | | |
| 14 | 1-{Benzyl-[2-(3,4-dimethoxyphenyl)-ethyl]-amino}-3-(4-benzyloxy-phenoxy)-propan-2-ol | 5.0 (N = 2) | 0.016 (N = 1) | |
| 15 | 1-{Benzyl-[2-(3,4-dimethoxyphenyl)-ethyl]-amino}-3-(4-cyclohexyl-2-methylphenoxy)-propan-2-ol | 9.2 (N = 1) | | |
| 16 | 1-{Benzyl-[2-(3,4-dimethoxyphenyl)-ethyl]-amino}-3-(indan-5-yloxy)-propan-2-ol | 4.8 (N = 2) | | |
| 17 | 1-{(2-Chlorobenzyl)-[2-(3,4-dimethoxyphenyl)-ethyl]-amino}-3-m-tolyloxy-propan-2-ol | 55% at 30 µM<br>46% at 10 µM | | |
| 18 | 1-{Benzyl-[2-(3,4-dimethoxyphenyl)-ethyl]-amino}-3-(naphthalen-1-yloxy)-propan-2-ol | 8.1 (N = 1) | | |
| 19 | 1-{Benzyl-[2-(3,4-dimethoxyphenyl)-ethyl]-amino}-3-(naphthalen-1-ylsulfanyl)-propan-2-ol | 2.5 (N = 2) | 0.2 | |
| 20 | 1-{Benzyl-[2-(3,4-dimethoxyphenyl)- | 4.7 (N = 1) | 0.62 (N = 1) | 11.5 |

TABLE 1-continued

Biological Activity of Compounds of Formula I

| Example | Compound | CaFl (μM) | BTX Binding (μM) | NaFl (μM) |
|---|---|---|---|---|
| | ethyl]-amino}-3-(3-trifluoromethyl-phenoxy)-propan-2-ol | | | |
| 21 | 1-{Benzyl-[2-(3,4-dimethoxyphenyl)-ethyl]-amino}-3-(3-trifluoromethyl-phenylsulfanyl)-propan-2-ol | 4.3 (N = 1) | 0.44 (N = 2) | |
| 22 | 1-{[2-(3,4-Dimethoxyphenyl)-ethyl]-phenethyl-amino}-3-m-tolyloxy-propan-2-ol | 1.4 (N = 1) | | |
| 23 | 1-{Cyclohexylmethyl-(2-(3,4-dimethoxyphenyl)-ethyl-amino}-3-m-tolyloxy-propan-2-ol | 1.9 (N = 1) | | |
| 24 | 1-(4-Cyclohexyl-2-methylphenoxy)-3-{[2-(3,4-dimethoxyphenyl)-ethyl]-methylamino}-propan-2-ol | 2.1 (N = 2) | 0.31 (N = 1) | 8.1 |
| 25 | 1-{[2-(3,4-Dimethoxyphenyl)-ethyl]-methylamino}-3-m-tolyloxy-propan-2-ol | 31% at 30 μM | | |
| 26 | 1-(4-Benzyloxyphenoxy)-3-{[2-(3,4-dimethoxy-phenyl)-ethyl]-methylamino}-propan-2-ol | 3.3 (N = 1) | | |
| 27 | 1-{[2-(3,4-Dimethoxyphenyl)-ethyl]-methylamino}-3-(indan-5-yloxy)-propan-2-ol | 69% at 30 μM 43% at 10 μM | | |
| 28 | 1-{[2-(3,4-Dimethoxyphenyl)-ethyl]-methylamino}-3-(naphthalen-1-yloxy)-propan-2-ol | 6.8 (N = 1) | | |
| 29 | 1-{[2-(3,4-Dimethoxyphenyl)-ethyl]-methylamino}-3-(naphthalen-1-ylsulfanyl)-propan-2-ol | 3.6 (N = 1) | | |
| 30 | 1-[[2-(3,4-Dimethoxyphenyl)-ethyl]-(1H-indol-3-ylmethyl)-amino]-3-m-tolyloxy-propan-2-ol | 4.5 (N = 1) | 0.015 (N = 2) | |

Maximal electroshock (MES) is a well-established screen in rodents for anticonvulsant activity and is a standard paradigm for predicting clinical efficacy for an antiepileptic drug (Krall, R. L., et al., *Epilepsia* 19:409–428 (1978)). Thus, the compounds of Formula I may be evaluated for anticonvulsant activity using the following protocol.

Anticonvulsant and Ataxia Screening in Mice

All experiments were conducted on male CF-1 mice (Charles River Laboratory, Portage, Mich.). The mice weighed 20 to 35 g and were allowed free access to food and water prior to testing. The compounds were dissolved in various solutions of up to 50% organic solvents and 50% buffered solutions. All doses were injected intravenously (IV) in a volume of 1.0 mL per 100 g of body weight using a 25-gauge needle and a 1 cc syringe. Doses of the compounds were calculated as the free base.

Three minutes, 30 minutes, and 1 hour postdose, the mice were subjected to the Inverted Screen test, a measurement of ataxia. Ataxia was scored in this test if a mouse could neither cling to the bottom nor climb to the top of a 4 inch square of wire mesh within 60 seconds of its inversion in one trial. Ataxia was recorded as the number of mice that fell off the inverted screen out of five. The compound was considered active if two of the five mice fell off the inverted screen.

Maximal electroshock was administered via corneal electrodes with an electroshock apparatus (Wahlquist Instrument Company) immediately following the inverted screen test. The stimulus consisted of a 50 mA current (100 mA peak-to-peak) and duration of 0.2 seconds. The protocol for the MES assay involved groups of five mice per dose at each time period postdose. Typically, compounds were tested at three doses (Table 2). The mice were sacrificed with carbon dioxide immediately after MES. Anticonvulsant data were recorded as the number of mice protected from MES out of five. Two out of five were considered active. The MES results for a representative compound of Formula I is shown in Table 2.

TABLE 2

Anticonvulsant Activity (MES) of
Example 24 (1-(4-Cyclohexyl-2-methyl-phenoxy)-3-{[2-(3,4-dimethoxyphenyl)-ethyl]-methylamino}-propan-2-ol

| | | 1 mg/kg (IV) | 3 mg/kg (IV) | 10 mg/kg (IV) |
|---|---|---|---|---|
| 3 min | MES | 0/5 | 0/5 | 4/5 |
| | Ataxia | 0/5 | 0/5 | 0/5 |
| 30 min | MES | 0/5 | 1/5 | 4/5 |
| | Ataxia | 0/5 | 0/5 | 1/5 |
| 1 hr | MES | NT[a] | 1/5 | 3/4[b] |
| | Ataxia | NT | 0/5 | 0/4 |

[a]NT = not tested
[b]1/5 Animals died in this group

Compounds of Formula I are prepared as outlined in Schemes 1 and 2.

SCHEME 1
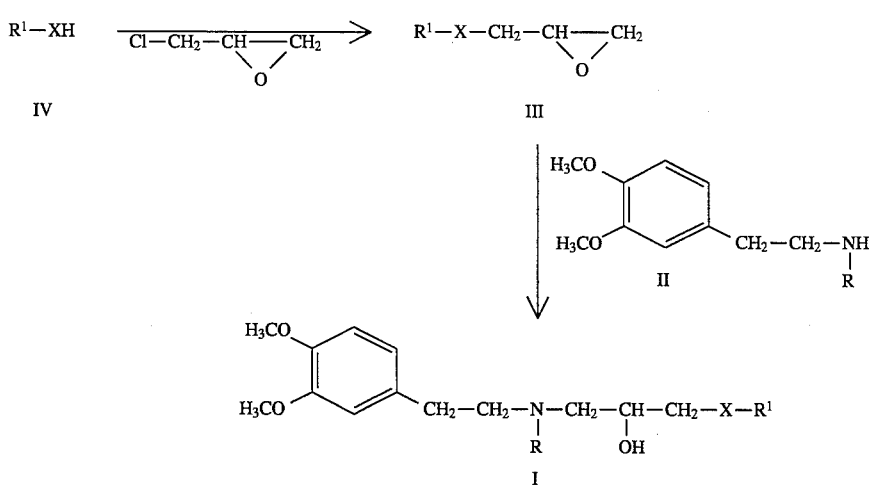
SCHEME 2
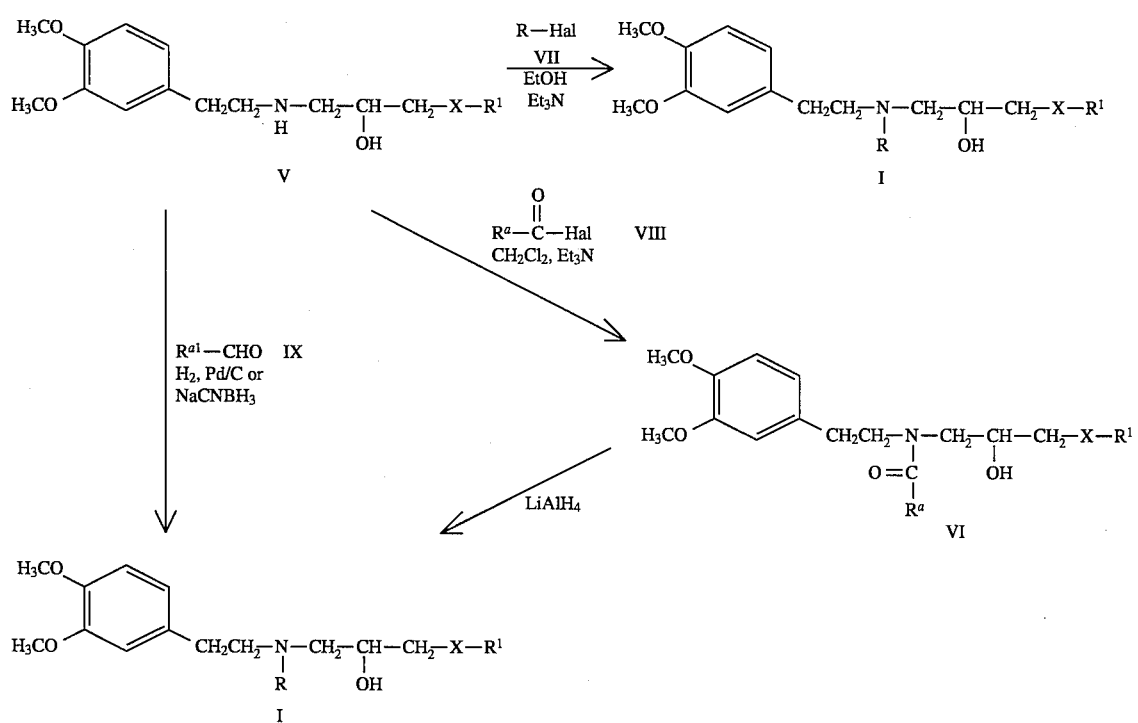
Reaction of a compound of Formula IV wherein R¹ is
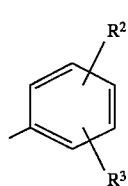
wherein
R² and R³ are each the same or different and each is hydrogen, alkyl, alkoxy, benzyloxy, cycloalkyl, halogen, or trifluoromethyl,
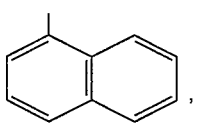
,
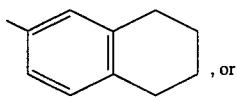
, or

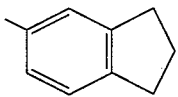

X is O or S with epichlorohydrin in a solvent such as, for example, 2-butanone and the like to afford a compound of Formula III wherein $R^1$ and X are as defined above. Preferably, the reaction is carried out in 2-butanone.

A compound of Formula III is reacted with a 3,4-dimethoxyphenethylamine of Formula II wherein R is alkyl, arylalkyl, cyclohexylmethyl, or indol-3-ylmethyl in the presence of a base such as, for example, an alkali metal carbonate, an alkaline earth metal carbonate such as, for example, sodium carbonate and the like, and a solvent such as, for example, acetonitrile and the like at about room temperature to about the reflux temperature of the solvent for about 1 hour to about 48 hours to afford a compound of Formula I wherein R, $R^1$, and X are as defined above. Preferably, the reaction is carried out in the presence of sodium carbonate in acetonitrile at about reflux temperature for about 48 hours.

Reaction of a compound of Formula V wherein $R^1$ and X are as defined above with a compound of formula R-Hal      VII wherein Hal is halogen and R is as defined above in the presence of a base such as, for example, triethylamine and the like, and a solvent such as, for example, absolute ethanol and the like at about room temperature to about the reflux temperature of the solvent for about 1 hour to about 18 hours to afford a compound of Formula I wherein R, $R^1$, and X are as defined above. Preferably, the reaction is carried out in the presence of triethylamine in absolute ethanol at about reflux temperature for about 18 hours.

Reaction of a compound of Formula V wherein $R^1$ and X are as defined above with a compound of formula

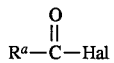
     VIII wherein $R^a$ is alkyl of from 1 to 5 carbon atoms, arylalkyl wherein alkyl is of from 1 to 5 carbon atoms, cyclohexyl or indol-3-yl, and Hal is as defined above in the presence of a base such as, for example, triethylamine and the like, and a solvent such as, for example, methylene chloride and the like at about room temperature for about 1 hour to about 24 hours to afford an amide of Formula VI wherein R, $R^1$ and X are as defined above. Preferably, the reaction is carried out in the presence of triethylamine in methylene chloride at about room temperature for about 24 hours.

Reaction of the amide of Formula VI with a hydride reagent such as, for example, lithium aluminum hydride and the like in a solvent such as, for example, diethyl ether and the like at about room temperature for about 1 hour to about 3 days to afford a compound of Formula I wherein R, $R^1$, and X are as defined above. Preferably, the reaction is carried out with lithium aluminum hydride in diethyl ether at about room temperature for about 3 days.

Reaction of a compound of Formula V wherein $R^1$ and X are as defined above with a compound of formula $R^{a1}$—CHO      IX wherein $R^{a1}$ is H, alkyl of from 1 to 5 carbon atoms, arylalkyl wherein alkyl is of from 1 to 5 carbon atoms, cyclohexyl, or indol-3-yl in a solvent such as, for example, methanol and the like and subsequent reaction with a hydride reagent such as, for example, sodium cyanoborohydride at about room temperature for about 3 hours to about 16 hours to afford a compound of Formula I wherein R, $R^1$ and X are as defined above. Preferably, the reaction is carried out in methanol and subsequently reacted with sodium cyanoborohydride at about room temperature for about 16 hours.

Reaction of a compound of Formula V with aqueous formaldehyde in the presence of hydrogen and a catalyst such as, for example, 10% palladium on carbon and the like in a solvent such as, for example, ethanol and the like at about room temperature for about 1 hour to about 4 hours to afford a compound of Formula I wherein R, $R^1$ and X are as defined above. Preferably the reaction is carried out with 10% palladium on carbon in ethanol at about room temperature for about 4 hours.

A compound of Formula V is prepared from a compound of Formula IIa

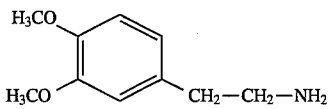
     IIa using the methodology used to prepare a compound of Formula I from a compound of Formula II.

Resolution of enantiomers of the various compounds of Formula I can be performed using conventional methodology such as, for example, by formation of chiral acid adducts followed by several recrystallizations.

Compounds of Formulas IIa, IV, VII, VIII, and IX are either known or can be prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the confounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5 or 10 to about 70% percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient-sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of epilepsy, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

1-[[2-(3,4-Dimethoxyphenyl)-ethyl]-(4-fluorobenzyl)amino]-3-m-tolyloxy-propan-2-ol, oxalate Step 1. Preparation of 2-m-Tolyloxy-methyl-oxirane m-Cresol (10.8 g, 0.10 mol) and epichlorohydrin (15.15 g, 0.16 mol) are suspended in 2-butanone and heated to reflux for 4 days. The reaction is filtered, and the solid is washed with acetone. The filtrate is concentrated in vacuo, and the residue is chromatographed on a silica gel column eluted with petroleum ether:ethyl acetate (9:1). The product is isolated as a clear oil.

Step 2. Preparation of 1-[2-(3,4-Dimethoxyphenyl)ethylamino] -3-m-tolyloxy-propan-2-ol 3,4-Dimethoxyphenethylamine (1.18 g, 0.0065 mol) and sodium carbonate ($Na_2CO_3$) (3 g) are combined in acetonitrile (40 mL). 2-m-Tolyloxy-methyl-oxirane (2 g, 0.01 mol) from Step 1 is added, and the reaction is stirred 18 hours at 25° C. The reaction is heated to reflux for 48 hours, and the excess carbonate is removed by filtration. The organics are concentrated in vacuo, and the residue is chromatographed on a silica gel column eluted with methylene chloride with increasing amounts of methanol up to 5%. The product is isolated as a yellow oil.

Step 3. Preparation of 1-[[2-(3,4-Dimethoxyphenyl)ethyl]-(4-fluorobenzyl)-amino]-3-m-tolyloxy-propan-2-ol, oxalate 1-[2-(3,4-Dimethoxyphenyl)-ethylamino]-3-m-tolyloxypropan- 2-ol from (1.5 g, 0.0039 mol) from Step 2, triethylamine (1.62 g, 0.016 mol), and 4-fluorobenzyl chloride (1.73 g, 0.012 mol) are combined in absolute ethanol (70 mL), and the reaction is refluxed for 18 hours. The reaction is concentrated in vacuo, and the crude residue is partitioned between methylene chloride and saturated sodium bicarbonate ($NaHCO_3$). The organic layer is dried over magnesium sulfate ($MgSO_4$), filtered, and concentrated to produce a thick oil which is chromatographed on a silica gel column eluted with petroleum ether with increasing amounts of ethyl acetate (EtOAc) up to 25%. The free base (1.68 g) is isolated as an oil which is dissolved in a minimum of methanol (MeOH). An ethereal solution of oxalic acid (0.36 g, 0.004 mol) is added to the methanol and the precipitate is collected by filtration. The oxalate salt is recrystallized from isopropyl alcohol to produce the title compound as a white solid; mp 125°–127° C.

In a process analogous to Example 1 using appropriate starting materials, the corresponding compounds of Formula I (Examples 2–21) are prepared as follows.

EXAMPLE 2

1-{Benzyl-[2-(3,4-dimethoxyphenyl)-ethyl]amino}-3-m-tolyloxy-propan-2-ol, oxalate; mp 131°–132° C.

EXAMPLE 3

1-{(4-Chlorobenzyl)-[2-(3,4-dimethoxyphenyl)-ethyl]-amino}-3-m-tolyloxy-propan-2-ol, oxalate; mp 117°–119° C.

EXAMPLE 4

1-[[2-(3,4-Dimethoxyphenyl)-ethyl]-(3-fluorobenzyl)amino]-3-m-tolyloxy-propan-2-ol, oxalate; mp 121°–123° C.

EXAMPLE 5

1-[[2-(3,4-Dimethoxyphenyl)-ethyl]-(4-nitrobenzyl)amino] -3-m-tolyloxy-propan-2-ol, oxalate; mp 157°–158° C.

EXAMPLE 6

1-[[2-(3,4-Dimethoxyphenyl)-ethyl]-(3-nitrobenzyl)amino] -3-m-tolyloxy-propan-2-ol, oxalate; mp 137°–139 ° C.

EXAMPLE 7

1-{(3-Chlorobenzyl)-[2-(3,4-dimethoxyphenyl)-ethyl]amino]-3-m-tolyloxy-propan-2-ol, oxalate; mp 125°–126° C.

EXAMPLE 8

1-[[2-(3,4-Dimethoxyphenyl)-ethyl]-(4-methoxybenzyl)amino]-3-m-tolyloxy-propan-2-ol, oxalate; mp 117°–118° C.

EXAMPLE 9

1-{[2-(3,4-Dimethoxyphenyl)-ethyl]-naphthalen-1-ylmethylamino}-3-m-tolyloxy-propan-2-ol, oxalate; mp 111°–113° C.

EXAMPLE 10

1-[[2-(3,4-Dimethoxyphenyl)-ethyl]-(3-methoxybenzyl)amino]-3-m-tolyloxy-propan-2-ol, oxalate; mp 144°–146° C.

EXAMPLE 11

1-[[2-(3,4-Dimethoxyphenyl)-ethyl]-(2-nitrobenzyl)amino]-3-m-tolyloxy-propan-2-ol, oxalate; mp 96°–99° C.

EXAMPLE 12

1-[[2-(3,4-Dimethoxyphenyl)-ethyl]-(2-methoxybenzyl)amino]-3-m-tolyloxy-propan-2-ol, oxalate; mp 69°–73° C.

EXAMPLE 13

1-[[2-(3,4-Dimethoxyphenyl)-ethyl]-(2-fluorobenzyl)amino]-3-m-tolyloxy-propan-2-ol, oxalate; mp <60° C. (foam).

EXAMPLE 14

1-{Benzyl-[2-(3,4-dimethoxyphenyl)-ethyl]-amino}-3 -(4-benzyloxyphenoxy)-propan-2-ol, oxalate; mp 136°–138° C.

EXAMPLE 15

1-{Benzyl-[2-(3,4-dimethoxyphenyl)-ethyl]-amino}-3 -(4-cyclohexyl-2-methylphenoxy)-propan-2-ol, oxalate; mp 135°–137° C.

EXAMPLE 16

1-{Benzyl-[2-(3,4-dimethoxyphenyl)-ethyl]-amino}-3 -(indan-5-yloxy)-propan-2-ol, oxalate; mp 151°–153° C.

EXAMPLE 17

1-{(2-Chlorobenzyl)- [2-(3,4-dimethoxyphenyl)-ethyl]amino}-3-m-tolyloxy-propan-2-ol, oxalate; mp <80° C. (foam).

EXAMPLE 18

1-{Benzyl-[2-(3,4-dimethoxyphenyl)-ethyl]-amino}-3 -(naphthalen-1-yloxy)-propan-2-ol, oxalate; mp 140°–142° C.

EXAMPLE 19

1-{Benzyl-[2-(3,4-dimethoxyphenyl)-ethyl]-amino}-3 -(naphthalen-1-ylsulfanyl)-propan-2-ol, oxalate; mp 78°–92° C.

EXAMPLE 20

1-{Benzyl-[2-(3,4-dimethoxyphenyl)-ethyl]-amino}-3-(3-trifluoromethylphenoxy)-propan-2-ol, oxalate; mp 147°–149° C.

EXAMPLE 21

1-{Benzyl-[2-(3,4-dimethoxyphenyl)-ethyl]-amino}-3 -(3-trifluoromethylphenylsulfanyl)-propan-2-ol, oxalate; mp 118°–121° C.

EXAMPLE 22

1-{[2-(3,4-Dimethoxyphenyl)-ethyl]-phenethylamino{-3-m-tolyloxy-propan-2-ol, oxalate Step 1. Preparation of N-[2-(3,4-Dimethoxyphenyl)ethyl]-N-(2-hydroxy-3-m-tolyloxy-propyl)-2-phenylacetamide 1-[2-(3,4-Dimethoxyphenyl)-ethylamino]-3-m-tolyloxy-propan- 2-ol (1.5 g, 0.0039 mol) from Example 1, Step 2 and triethylamine (0.81 g, 0.008 mol) are dissolved in methylene chloride (100 mL) and phenylacetyl chloride (0.62 g, 0.004 mol) is added dropwise. The reaction is stirred for 24 hours and extracted with 5% sodium bicarbonate (50 mL), 1N hydrochloric acid (50 mL) and water (50 mL). The methylene chloride layer is dried over magnesium sulfate, filtered, and concentrated to yield a viscous yellow oil (1.74 g) which is one product by thin layer chromatography [silica gel eluted with ethyl acetate:petroleum ether (3:7)]. The amide is used in the next step without additional purification.

Step 2. Preparation of 1-{[2-(3,4-Dimethoxyphenyl)ethyl]-phenethylamino}-3-m-tolyloxy-propan-2-ol, oxalate Lithium aluminum hydride pellets (1.62 g, 0.0043 mol) are suspended in anhydrous diethyl ether (Et$_2$O) (50 mL). The amide (1.7 g, 0.0038 mol) is dissolved in diethyl ether (20 mL) and added dropwise to the lithium aluminum hydride suspension over a 30 minute period. The reaction is stirred for 3 days and a saturated solution of potassium sodium tartrate is added to the reaction to quench it. The diethyl ether layer is washed with saturated sodium chloride (NaCl) (50 mL), dried over magnesium sulfate, filtered, and concentrated. The free base is converted to the oxalate salt using oxalic acid (0.25 g) and the salt recrystallized from MeOH/Et$_2$O to yield the title compound as a white solid (0.95 g, mp 81°–84° C.).

EXAMPLE 23

1-{Cyclohexylmethyl-[2-(dimethoxyphenyl)-ethyl]-amino}-3-m-tolyloxy-propan-2-ol, oxalate 1-[2-(3,4-Dimethoxyphenyl)-ethylamino]-3-m-tolyloxy-propan- 2-ol from Example 1, Step 2 (1.5 g, 0.0039 mol) is dissolved in methanol (80 mL). Cyclohexanecarboxaldehyde (0.66 g, 0.0058 mol) is added to the methanolic solution, and the reaction is stirred for 3 hours. Sodium cyanoborohydride (0.49 g, 0.0078 mol) is then added, and the reaction is stirred for an additional 16 hours. The reaction is concentrated in vacuo, and the residue is partitioned between methylene chloride and 5% sodium bicarbonate solution. The methylene chloride layer is dried over magnesium sulfate, filtered, concentrated, and the crude product is chromatographed on silica gel column eluted with ethyl acetate:petroleum ether (1:4) to yield the title compound as a clear oil (0.4 g). The free base of the amine is converted to the oxalate salt using oxalic acid (67 mg). The salt is isolated as a white solid (0.35 g, mp 139°–141° C.) after recrystallization from MeOH/Et$_2$O.

EXAMPLE 24

1-(4-Cyclohexyl-2-methylphenoxy)-3-{[2-(3,4 -dimethoxyphenyl)-ethyl]-methylamino}-propan-2-ol, oxalate 1-(4-Cyclohexyl-2-methyl-phenoxy)-3-[2-(3,4 -dimethoxyphenyl)-ethylamino]-propan-2-ol (1.12 g, 0.0026 mol) is dissolved in ethanol (70 mL) and treated with aqueous formaldehyde (5 mL) and 10% palladium on carbon (Pd/c) (0.2 g). The reaction is hydrogenated at an initial pressure of 52 pounds per square inch (psi) for 4 hours. The reaction is filtered, and the volatiles are removed in vacuo. The oily residue is converted to the oxalate salt by treatment with oxalic acid (0.29 g) and crystallization from MeOH/Et$_2$O to yield the title confound as a white solid (1.21 g, mp 108°–110° C.).

In a process analogous to Example 24 using appropriate starting materials, the corresponding compounds of Formula I (Examples 25–29) are prepared as follows.

EXAMPLE 25

1-{[2-(3,4-Dimethoxyphenyl)-ethyl]-methylamino}-3 -m-tolyloxy-propan-2-ol, mp 147°–148° C.

EXAMPLE 26

1-(4-Benzyloxyphenoxy)-3-{[2-(3,4-dimethoxyphenyl)ethyl]-methylamino}-propan-2-ol, oxalate; mp 120°–122 ° C.

EXAMPLE 27

1-{[2-(3,4-Dimethoxyphenyl)-ethyl]-methylamino}-3-indan-5-yloxy)propan-2-ol, oxalate; mp 131°–134° C.

EXAMPLE 28

1-{[2-(3,4-Dimethoxyphenyl)-ethyl]-methylamino}-3-(naphthalen-1-yloxy)-propan-2-ol, oxalate; mp 155°–157° C.

EXAMPLE 29

1-{[2-(3,4-Dimethoxyphenyl)-ethyl]-methylamino}-3 -(naphthalen-1-ylsulfanyl)-propan-2-ol, oxalate; mp 137°–139 ° C.

EXAMPLE 30

1-[[2-(3,4-Dimethoxyphenyl)-ethyl-(1H-indol-3 -ylmethyl)-amino]-3-m-tolyloxy-propan-2-ol, oxalate Step 1. Preparation of 3-Formyl-indole-1-carboxylic acid, tert-butyl ester 1H-Indole-3-carboxaldehyde (25 g, 0.172 mol) is dissolved in a mixture of tetrahydrofuran/water (7:3, 500 mL) and 1N potassium hydroxide (60 mL) is added. Di-tert-butyl-dicarbonate (41.3 g, 0.189 mol) is dissolved in tetrahydrofuran (60 mL) and is added dropwise to the reaction solution over a 2-hour period. The reaction is stirred at 25° C. for 3 days. The reaction is extracted with ethyl acetate (500 mL), dried over magnesium sulfate, filtered, and concentrated in vacuo. The crude product is purified by chromatography on silica gel eluted initially with methylene chloride with increasing amounts of methanol up to 5%. The Boc-protected indole is used without additional purification.

Step 2. Preparation of 3-{[[2-(3,4-Dimethoxyphenyl)ethyl] -(2-hydroxy-3-m-tolyloxy-propyl)-amino]-methyl}-indole-1-carboxylic acid, tert-butyl ester 1-[2-(3,4-Dimethoxyphenyl)-ethylamino]-3 -m-tolyloxypropan-2-ol (1.27 g, 2.9 mmol) (Example 1, Step 2) and the 3-formyl-indole-1-carboxylic acid, tert-butyl ester (1.06 g, 4.3 mmol) (Example 30, Step 1) are combined in methanol (70 mL) and stirred for 3 hours. Sodium cyanoborohydride (0.36 g, 5.8 mmol) is added in small batches, and the reaction is stirred at 25° C. for 16 hours. The reaction is concentrated in vacuo, and the residue is partitioned between methylene chloride and 5% sodium bicarbonate solution. The methylene chloride layer is dried over magnesium sulfate, filtered, and concentrated. The crude product is chromatographed on silica gel eluted with ethyl acetate/ petroleum ether (3:7) to yield the product as a yellow oil (1.34 g) which is used without additional purification.

Step 3. Preparation of 1-[[2-(3,4-Dimethoxyphenyl)ethyl]-(1H-indol-3-ylmethyl)-amino]-3-m-tolyloxypropan-2-ol, oxalate 3-{[[2-(3,4-Dimethoxyphenyl)-ethyl]-(2-hydroxy-3 -m-tolyloxy-propyl)-amino]-methyl}-indole-1-carboxylic acid, tert-butyl ester (1.34 g, 2.3 mmol) is dissolved in methylene chloride (12 mL) and trifluoroacetic acid (12 mL). The reaction turned bright red and is stirred for 18 hours. The reaction is concentrated in vacuo, and the crude product is chromatographed on silica gel eluted initially with methylene chloride followed by methylene chloride/methanol with increasing quantities of methanol up to 20%. The free base is isolated as a purple foam which is converted to the oxalate salt using oxalic acid (0.11 g) in methanol/diethyl ether to produce the salt as a beige solid; mp 130°–132° C.

What is claimed is:

1. A compound of Formula I

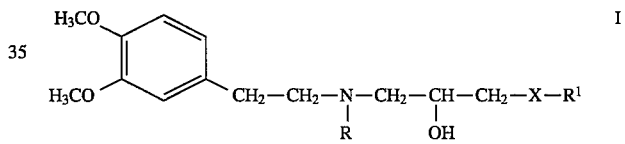

wherein

R is alkyl, arylalkyl, cyclohexylmethyl, or indol-3-ylmethyl;

R$^1$ is

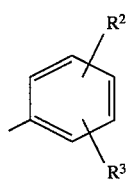

wherein

R$^2$ and R$^3$ are each the same or different and each is alkyl, benzyloxy, cycloalkyl, halogen, or trifluoromethyl,

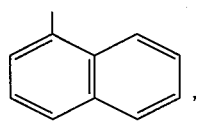,

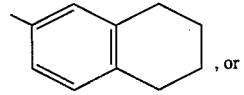, or

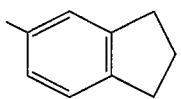

X is O or S; and isomers thereof; or a pharmaceutically acceptable salt thereof, provided that when R is —CH$_2$-Phenyl, R$^1$ is other than

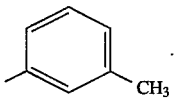

2. A compound according to claim 1 in which
R is methyl, arylalkyl, cyclohexylmethyl, or indol-3-ylmethyl;
R$^1$ is

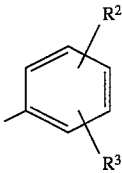

wherein
R$^2$ and R$^3$ are each the same or different and each is alkyl, benzyloxy, cycloalkyl, or trifluoromethyl,

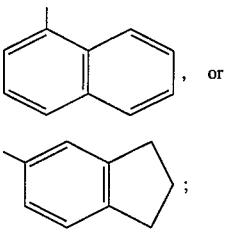

X is O or S, provided that when R is —CH$_2$-Phenyl, R$^1$ is other than

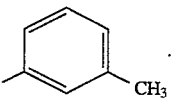

3. A compound according to claim 2 selected from the group consisting of:
1-[[2-(3,4-Dimethoxyphenyl)-ethyl]-(4-fluorobenzyl)amino]-3-m-tolyloxy-propan-2-ol;
1-{(4-Chlorobenzyl-[2-(3,4-dimethoxyphenyl-ethyl]amino}-3-m-tolyloxy-propan-2-ol;
1-[[2-(3,4-Dimethoxyphenyl)-ethyl]-(3-fluorobenzyl)amino]-3-m-tolyloxy-propan-2-ol;
1-[[2-(3,4-Dimethoxyphenyl)-ethyl]-(4-nitrobenzyl)amino]-3 -m-tolyloxy-propan-2-ol;
1-[[2-(3,4-Dimethoxyphenyl)-ethyl]-(3-nitrobenzyl)amino]-3-m-tolyloxy-propan-2-ol;
1-{(3-Chlorobenzyl)-[2-(3,4-dimethoxyphenyl)-ethyl]amino}-3-m-tolyloxy-propan-2-ol;

1-[[2-(3,4-Dimethoxyphenyl)-ethyl]-(4-methoxybenzyl)amino]-3-m-tolyloxy-propan-2-ol;
1-{[2-(3,4-Dimethoxyphenyl)-ethyl]-naphthalen-1-ylmethylamino}-3-m-tolyloxy-propan-2-ol;
1-[[2-(3,4-Dimethoxyphenyl)-ethyl]-(3-methoxybenzyl)amino]-3-m-tolyloxy-propan-2-ol;
1-[[2-(3,4-Dimethoxyphenyl)-ethyl]-(2-nitrobenzyl)amino]-3-m-tolyloxy-propan-2-ol;
1-[[2-(3,4-Dimethoxyphenyl)-ethyl]-(2-methoxybenzyl)amino]-3-m-tolyloxy-propan-2-ol;
1-[[2-(3,4-Dimethoxyphenyl)-ethyl]-(2-fluorobenzyl)amino]-3-m-tolyloxy-propan-2-ol;
1-{Benzyl-[2-(3,4-dimethoxyphenyl)-ethyl]-amino}-3 -(4-benzyloxyphenoxy)-propan-2-ol;
1-{Benzyl-[2-(3,4-dimethoxyphenyl)-ethyl]-amino}-3 -(4-cyclohexyl-2-methylphenoxy)-propan-2-ol;
1-{Benzyl-[2-(3,4-dimethoxyphenyl)-ethyl]-amino}-3 -(indan-5-yloxy)-propan-2-ol;
1-{(2-Chlorobenzyl)-[2-(3,4-dimethoxyphenyl)-ethyl]amino}-3-m-tolyloxy-propan-2-ol;
1-{Benzyl-[2-(3,4-dimethoxyphenyl)-ethyl]-amino}-3 -(naphthalen-1-yloxy)-propan-2-ol;
1-{Benzyl-[2-(3,4-dimethoxyphenyl)-ethyl]-amino}-3-(naphthalen-1-ylsulfanyl)-propan-2-ol;
1-{Benzyl-[2-(3,4-dimethoxyphenyl)-ethyl]-amino}-3-(3-trifluoromethylphenoxy)-propan-2-ol;
1-{Benzyl-[2-(3,4-dimethoxyphenyl)-ethyl]-amino}-3-(3-trifluoromethylphenylsulfanyl)-propan-2-ol;
1-{[2-(3,4-Dimethoxyphenyl)-ethyl]-phenethyl-amino}-3-m-tolyloxy-propan-2-ol;
1-{Cyclohexylmethyl-[2-(3,4-dimethoxyphenyl)-ethyl]-amino}-3-m-tolyloxy-propan-2-ol;
1-(4-Cyclohexyl-2-methylphenoxy)-3-{[2 -(3,4-dimethoxyphenyl)-ethyl]-methylamino}-propan-2-ol;
1-{[2-(3,4-Dimethoxyphenyl)-ethyl]-methylamino}-3 -m-tolyloxy-propan-2-ol;
1-(4-Benzyloxyphenoxy)-3-{[2-(3,4-dimethoxy-phenyl)ethyl]-methylamino}-propan-2-ol;
1-{[2-(3,4-Dimethoxyphenyl)-ethyl]-methylamino} -3-(indan-5-yloxy)-propan-2-ol;
1-{[2-(3,4-Dimethoxyphenyl)-ethyl]-methylamino} -3-(naphthalen-1-yloxy)-propan-2-ol;
1-{[2-(3,4-Dimethoxyphenyl)-ethyl]-methylamino} -3-(naphthalen-1-ylsulfanyl)-propan-2-ol; and
1-[[2-(3,4-Dimethoxyphenyl)-ethyl]-(1H-indol-3-ylmethyl)-amino]-3-m-tolyloxy-propan-2-ol; isomers thereof;
or a pharmaceutically acceptable salt thereof.

4. A compound according to claim 3 selected from the group consisting of:
1-(4-Cyclohexyl-2-methylphenoxy)-3-{[2-(3,4 -dimethoxyphenyl)-ethyl]-methylamino}-propan-2-ol;
1-{Benzyl-[2-(3,4-dimethoxyphenyl)-ethyl] amino}-3-(4-cyclohexyl-2-methylphenoxy)-propan-2-ol; and
1-{Cyclohexylmethyl-2-(3,4-dimethoxyphenyl)ethyl]-amino}-3-m-tolyloxy-propan-2-ol; or a pharmaceutically acceptable salt thereof.

5. A method of treating epilepsy comprising administering to a host suffering therefrom a therapeutic effective amount of a compound of Formula I

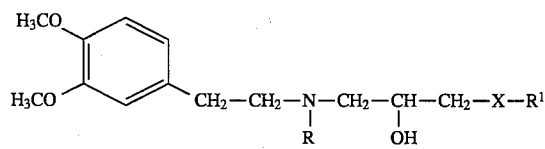

wherein

R is alkyl, arylalkyl, cyclohexylmethyl, or indol-3-ylmethyl;

$R^1$ is

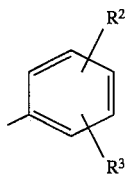

wherein $R^2$ and $R^3$ are each the same or different and each is hydrogen, alkyl, alkoxy, benzyloxy, cycloalkyl, halogen, or trifluoromethyl,

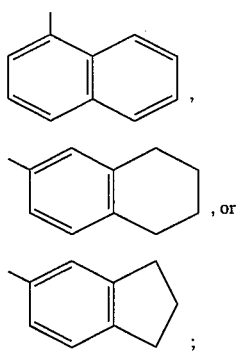

X is O or S; and isomers thereof; or a pharmaceutically acceptable salt thereof.

6. A pharmaceutical composition comprising a therapeutic effective amount of a compound according to claim 1 in admixture with a pharmaceutically acceptable excipient, diluent, or carrier.

7. A pharmaceutical composition adapted for administration as an agent for treating epilepsy comprising a therapeutic effective amount of a compound according to claim 1 in admixture with a pharmaceutically acceptable excipient, diluent, or carrier.

* * * * *